United States Patent
Kurunczi

(10) Patent No.: US 7,094,314 B2
(45) Date of Patent: Aug. 22, 2006

(54) ATMOSPHERIC PRESSURE NON-THERMAL PLASMA DEVICE TO CLEAN AND STERILIZE THE SURFACES OF PROBES, CANNULAS, PIN TOOLS, PIPETTES AND SPRAY HEADS

(75) Inventor: Peter Frank Kurunczi, Weehawken, NJ (US)

(73) Assignee: Cerionx, Inc., Pennsauken, NJ (US)

( * ) Notice: Subject to any disclaimer, the term of this patent is extended or adjusted under 35 U.S.C. 154(b) by 0 days.

(21) Appl. No.: 10/858,272

(22) Filed: Jun. 1, 2004

(65) Prior Publication Data
US 2005/0005948 A1    Jan. 13, 2005

Related U.S. Application Data

(60) Provisional application No. 60/478,418, filed on Jun. 16, 2003.

(51) Int. Cl.
*C23F 1/00* (2006.01)
*B23K 15/00* (2006.01)

(52) U.S. Cl. .......................... 156/345.44; 156/345.43; 156/345.48; 219/121.11

(58) Field of Classification Search .......... 156/345.43, 156/345.48, 345.44; 219/121.59, 121.4, 219/121.11
See application file for complete search history.

(56) References Cited

U.S. PATENT DOCUMENTS

| | | | |
|---|---|---|---|
| 5,099,100 A * | 3/1992 | Bersin et al. ............ 219/121.4 |
| 5,133,986 A * | 7/1992 | Blum et al. .................. 427/569 |
| 5,200,158 A | 4/1993 | Jacob |
| 5,225,659 A * | 7/1993 | Kusano et al. ......... 219/121.59 |
| 5,236,672 A | 8/1993 | Nunez et al. |
| 5,262,125 A | 11/1993 | Goodman |
| 5,286,532 A * | 2/1994 | Yoshikawa et al. ......... 427/536 |
| 5,292,396 A * | 3/1994 | Takashima et al. .... 156/345.43 |
| 5,414,324 A | 5/1995 | Roth et al. |
| 5,451,428 A | 9/1995 | Rupp |
| 5,573,732 A | 11/1996 | Waggener et al. |
| 5,633,424 A | 5/1997 | Graves et al. |
| 5,686,789 A | 11/1997 | Schoenbach et al. |
| 5,700,327 A | 12/1997 | Babacz et al. |
| 5,741,460 A | 4/1998 | Jacob et al. |
| 5,876,663 A | 3/1999 | Laroussi |
| 5,895,558 A | 4/1999 | Spence |
| 5,897,831 A | 4/1999 | Jacob et al. |
| 5,935,330 A | 8/1999 | Taniguchi |
| 5,939,829 A | 8/1999 | Schoenbach et al. |
| 5,965,093 A | 10/1999 | Adams |
| 6,059,935 A | 5/2000 | Spence |
| 6,072,273 A | 6/2000 | Schoenbach et al. |
| 6,105,589 A | 8/2000 | Vane |

(Continued)

FOREIGN PATENT DOCUMENTS

EP    0798 397 A2 *    10/1997

OTHER PUBLICATIONS

U. Kogelschatz, "Dielectric-Barrier Discharges: Their History, Discharge Physics and Industrial Applications," Plasma Chemistry and Plasma Processing, vol. 23, No. 1, Mar. 2003.

(Continued)

*Primary Examiner*—M. Kornakov
(74) *Attorney, Agent, or Firm*—Moser IP Law Group

(57) ABSTRACT

The present invention relates to methods and apparatuses for the use of atmospheric pressure non-thermal plasma to clean and sterilize the surfaces of liquid handling devices.

13 Claims, 3 Drawing Sheets

U.S. PATENT DOCUMENTS

| | | |
|---|---|---|
| 6,174,500 B1 | 1/2001 | Uno et al. |
| 6,204,605 B1 | 3/2001 | Laroussi et al. |
| 6,342,187 B1 | 1/2002 | Jacob et al. |
| 6,346,770 B1 | 2/2002 | Schoenbach et al. |
| 6,403,029 B1 | 6/2002 | Schmidt |
| 6,482,369 B1 | 11/2002 | Wang |
| 6,518,692 B1 | 2/2003 | Schoenbach et al. |
| 6,528,022 B1 | 3/2003 | Kinoshita |
| 6,610,257 B1 | 8/2003 | Vane |
| 6,624,413 B1 | 9/2003 | Klein |
| 6,645,441 B1 | 11/2003 | Andrews et al. |
| 6,652,816 B1 | 11/2003 | Hwang |
| 6,667,007 B1 | 12/2003 | Schmidt |
| 6,692,704 B1 | 2/2004 | Nelson et al. |
| 6,724,608 B1 | 4/2004 | Hensley et al. |
| 6,784,424 B1 | 8/2004 | Willoughby et al. |
| 2001/0031234 A1 | 10/2001 | Christodoulatos et al. |
| 2002/0020691 A1 | 2/2002 | Jewett et al. |
| 2002/0036461 A1 | 3/2002 | Schoenbach et al. |
| 2002/0076369 A1 | 6/2002 | Hwang |
| 2002/0076370 A1 | 6/2002 | Wong et al. |
| 2002/0153241 A1 | 10/2002 | Niv et al. |
| 2002/0195950 A1 | 12/2002 | Mikhael et al. |
| 2003/0015415 A1 | 1/2003 | Platt, Jr. et al. |
| 2003/0052096 A1 | 3/2003 | Crowe et al. |
| 2003/0072675 A1 | 4/2003 | Takeda et al. |
| 2003/0098230 A1 | 5/2003 | Carlow et al. |
| 2003/0106788 A1 | 6/2003 | Babko-Malyi |
| 2003/0116541 A1 | 6/2003 | Chiou et al. |
| 2003/0129107 A1 | 7/2003 | Denes et al. |
| 2003/0132100 A1 | 7/2003 | Crowe et al. |
| 2003/0155332 A1 | 8/2003 | Datta et al. |
| 2004/0011764 A1 | 1/2004 | DeVries et al. |
| 2004/0022945 A1 | 2/2004 | Goodwin et al. |
| 2004/0037756 A1 | 2/2004 | Houston, Jr. et al. |
| 2004/0045806 A1 | 3/2004 | Neff et al. |
| 2004/0050685 A1 | 3/2004 | Yara et al. |
| 2004/0052028 A1 | 3/2004 | O'Reilly et al. |
| 2004/0112537 A1 | 6/2004 | Yamazaki et al. |
| 2004/0134890 A1 | 7/2004 | Uhm et al. |
| 2004/0148860 A1 | 8/2004 | Fletcher |
| 2004/0185396 A1 | 9/2004 | Rosocha et al. |
| 2004/0195088 A1 | 10/2004 | Rostaing et al. |
| 2004/0231926 A1 | 11/2004 | Sakhrani et al. |
| 2004/0238124 A1 | 12/2004 | Nakamura |

OTHER PUBLICATIONS

U. Kogelschatz, "Filamentary, Patterned and Diffuse Barrier Discharges," IEEE Transactions on Plasma Science, vol. 30, No. 4, Aug. 2002.

N. St. J. Braithwaite, "Introduction to Gas Discharges" Plasma Sources Science and Technology, vol. 9, 2000, p517-527.

U. Kogelschatz et al. "Dielectric-Barrier Discharges, Principles and Applications" J. Phys IV France, 7, 1997, C4-47.

E. M. Van Veldhuizen, W.R. Rutgers. "Corona Discharges: Fundamentals and Diagnostics" Invited Paper, Proceedings of Frontiers in Low Temperature Plasma Diagnostics IV, Rolduc, The Netherlands, Mar. 2001, pp. 40-49.

Publication ANSI/SBS 4-2004, "Well Positions for Microplates," Jan. 2004, The Society for Biomolecular Screening, www.sbsonline.com.

H. Conrads et al., "Plasma Generation and Plasma Sources" Plasma Sources Science and Technology, vol. 9, 2000, p441-454.

* cited by examiner

ATMOSPHERIC PRESSURE NON-THERMAL PLASMA DEVICE TO CLEAN AND STERILIZE THE SURFACES OF PROBES, CANNULAS, PIN TOOLS, PIPETTES AND SPRAY HEADS

CROSS-REFERENCE TO RELATED APPLICATIONS

This application is entitled to priority pursuant to 35 U.S.C. §119(e) to U.S. provisional patent application No. 60/478,418, which was filed on Jun. 16, 2003. This application also claims priority to International Application No. PCT/US2004/017223 entitled "Atmospheric Pressure Non-Thermal Plasma Device to Clean and Sterilize the Surfaces of Probes, Cannulas, Pin Tools, Pipettes and Spray Heads" by inventor Peter Kurunczi, filed on May 28, 2004.

BACKGROUND OF THE INVENTION

Within the disciplines of the clinical, industrial and life science laboratory, scientists perform methods and protocols with extremely small quantities of fluids. These fluids consist of many categories and types with various physical properties. Frequently, volumes are worked with that are between a drop (about 25 microliters) and a few nanoliters. There are a number of standard methods employed to transfer liquid compounds from a source by aspirating the liquid from such fluid holding devices into a fluid handling device having a probe, cannula, pin tool or other similar component or plurality of components which move, manually or robotically, and then dispensing, from the same probe or plurality of probes, into another fluid holding device.

Four common techniques are (1) a scheme using a probe or cannula, that may or may not be coated with a layer of material or special coating, which is attached directly or by a tube to a pumping device, (2) a scheme using a disposable pipette instead of the probe/cannula but otherwise similar, (3) a scheme using a spray head with one or a plurality of openings and pumping system that physically propels multiple precisely metered microdroplets, and (4) a scheme using metal shafts with precisely machined hollowed out spaces at their ends that hold the fluid by surface tension (commonly referred to as a "pin tool").

As routine a process as fluid transfer is in the laboratory, technical challenges remain to achieve suitable levels of cleanliness of the dispensing devices. Currently the fluid handling devices undergo a "tip wash" process wherein they are cleansed in between use with a liquid solvent, such as DMSO or water. After the "tip wash" process, the used and now contaminated liquids must then be properly disposed of with respect to the required environmental regulations. As an alternative to this wet "tip wash" process, atmospheric pressure plasma can be used to replace the liquid cleaning process with a "dry" plasma cleaning process, thus eliminating the need for the handling and disposal of solvents that are biohazards and environmentally unfriendly.

The term "plasma" is generally used to denote the region in an electric gas discharge that has an equal number of positive ions and negative electrons (N. St. J. Braithwaite, "Introduction to gas discharges" Plasma Sources Science and Technology, V9, 2000, p517–527; H. Conrads et al., "Plasma Generation and Plasma Sources" Plasma Sources Science and Technology, V9, 2000, p441–454). A non-thermal, or non-equilibrium, plasma is one in which the temperature of the plasma electrons is higher than the temperature of the ionic and neutral species. Within an atmospheric pressure non-thermal plasma there is typically an abundance of other energetic and reactive particles, such as ultraviolet photons, excited and/or metastable atoms and molecules, and free radicals. For example, within an air plasma, there are excited and metastable species of $N_2$, N, $O_2$, O, free radicals such as OH, NO, O, and $O_3$, and ultraviolet photons ranging in wavelengths from 200 to 400 nanometers resulting from $N_2$, NO, and OH emissions.

The "dry" plasma cleaning process is achieved by exposing the surfaces of the fluid handling devices or other components to the atmospheric pressure plasma. The above mentioned reactive and energetic components can now interact with any contaminants on the surfaces, thereby volatizing, dissociating, and reacting with the contaminants, to form smaller and benign gaseous compounds that are vented off through the plasma cleaning device.

In addition to removing various unwanted compounds, the plasma can also be used to sterilize the surfaces of the fluid handling devices. The same ultraviolet photons, especially those with wavelengths below 300 nm, the free radicals and metastable molecules, and the plasma electrons and ions, provide a very harsh environment in which bacteria, viruses, fungi and their corresponding spores are lysed or otherwise rendered non-viable and either partially or completely volatized into gaseous compounds.

SUMMARY OF THE INVENTION

In one embodiment, the present invention features an apparatus for cleaning a fluid handling device. In one embodiment, the apparatus includes an array of channels, each made of a dielectric material and configured to accommodate a single fluid handling device, at least one electrode in contact with each channel for producing a discrete plasma in each channel, and at least one conducting ground adjacent to the array of channels. In one aspect, an apparatus of the invention has at least one conducting ground adjacent to each of the channels. In another aspect of the invention, a fluid handling device is the conducting ground. In yet another aspect, a fluid handling device forms a conducting ground.

In an embodiment of the invention, a plasma is produced in a plasma cleaning apparatus by applying a voltage in the range from about 5000 Volts to 15000 Volts.

In one embodiment of the invention, a channel of a plasma cleaning apparatus is cylindrical. In another embodiment, a channel of a plasma cleaning apparatus is rectangular. In one aspect of the invention, a channel of a plasma cleaning apparatus is closed on one end. In another aspect, a channel of a plasma cleaning apparatus is open on both ends.

In one embodiment, the present invention features a plasma cleaning apparatus that is in direct communication with a vacuum source.

In an embodiment of the present invention, an apparatus may contain an array of plasma cleaning apparatuses. In one aspect, an array of plasma cleaning apparatuses is in an arrangement corresponding to a microtiter plate format.

In one embodiment, the present invention features a plasma cleaning apparatus containing at least one rare gas.

In an embodiment, the present invention features an apparatus for cleaning a fluid handling device, wherein the apparatus contains an array of channels in a configuration corresponding to a microtiter plate. In one embodiment, each channel includes a dielectric material and is configured to accommodate a single fluid handling device. In one aspect, there is at least one electrode in contact with each channel for producing a discrete plasma in each channel and, additionally, there is a continuous conducting ground adjacent to the array of channels. In one embodiment, the channels of an apparatus of the invention are cylindrical. In another embodiment, the channels of an apparatus of the invention are rectangular.

The present invention also features, in one embodiment, an apparatus for cleaning a fluid handling device, wherein the apparatus contains an array of channels in a configuration corresponding to a microtiter plate, further wherein each channel consists of a dielectric material and is configured to accommodate a single fluid handling device. In one aspect, there is at least one electrode in contact with each channel for producing a discrete plasma in each channel and additionally, there is a conducting ground adjacent to each channel. In one aspect, a fluid handing device forms the conducting ground for the channel in which the device is accommodated. In one embodiment, the channels of an apparatus of the invention are cylindrical. In another embodiment, the channels of an apparatus of the invention are rectangular.

In an embodiment of the invention, a fluid handling device is inserted into a channel of a plasma cleaning apparatus such that the tip of the fluid handling device is located at about the center of the plasma field.

In one embodiment, the present invention features a method of cleaning a fluid handling device by positioning at least a portion of a fluid handling device within the interior of a channel of a plasma cleaning apparatus of the invention and forming a plasma within the interior of each channel in order to clean the fluid handling device. In one aspect, the invention features a method of cleaning a plurality of fluid handling devices by positioning at least a portion of each of a plurality fluid handling devices within the interior of a discrete channel of a plasma cleaning apparatus and forming a plasma within the interior of each of the discrete channels to clean the plurality of fluid handling devices.

BRIEF DESCRIPTION OF THE DRAWINGS

The accompanying drawings, which are incorporated herein and constitute a part of this specification, illustrate the presently preferred embodiments of the invention and, together with the general description given above and the detailed description given below, serve to explain the features of the invention. Some aspects of the drawings are not labeled, but are included to provide further details of the invention. Further, in some drawings, if a feature is present more than once in a drawing, the feature may be referenced only once.

In the drawings.

DETAILED DESCRIPTION OF THE INVENTION

Figure 1:
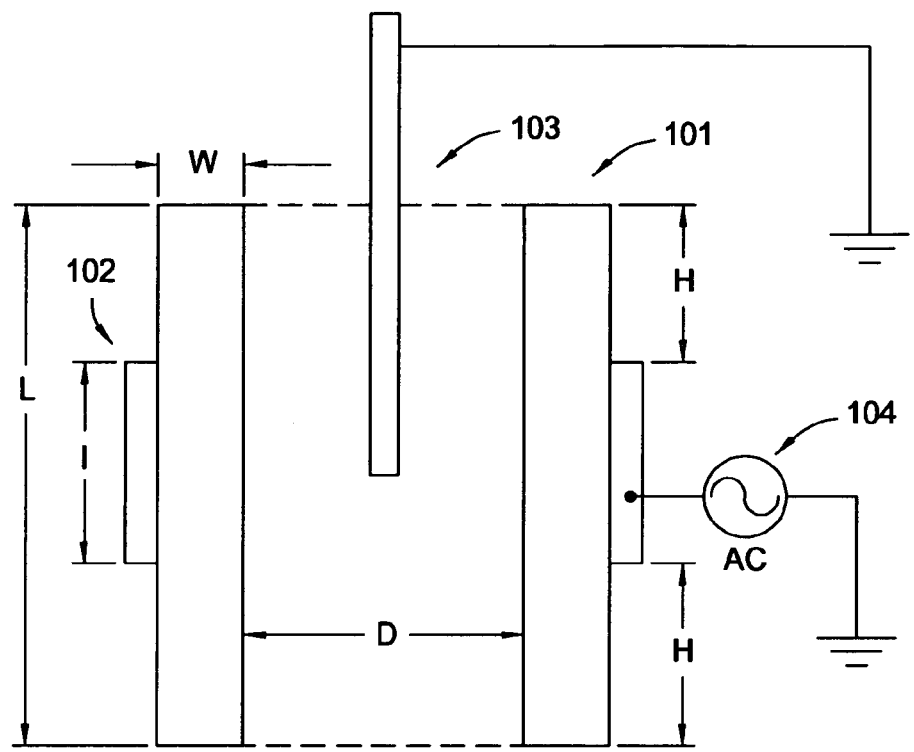
FIG. 1 is a cross section view of one embodiment of an atmospheric pressure plasma-based cleaning device of the invention.

In certain embodiments of the design of an atmospheric pressure plasma device according to the present invention, a dielectric barrier discharge (also known as a "silent discharge") scheme is used, where at least one electrode to which an alternating voltage is applied, includes an insulating dielectric (U. Kogelschatz et al. "Dielectric-Barrier Discharges, Principles and Applications" J. Phys IV France, 7, 1997, C4–47). The electrodes may comprise any conductive material. In one embodiment, a metal may be used. Metals useful in the present invention include, but are not limited to, copper, silver, aluminum, and combinations thereof. In another embodiment of the invention, an alloy of metals may be used as the electrode. Alloys useful in the present invention include, but are not limited to stainless steel, brass, and bronze. In another embodiment of the invention, a conductive compound may be used. Conductive compounds useful in the present invention include, but are not limited to indium-tin-oxide.

In one embodiment, an electrode of the invention may be formed using any method known in the art. In an embodiment of the invention, an electrode may be formed using a foil. In another embodiment of the invention, an electrode may be formed using a wire. In yet another embodiment of the invention, an electrode may be formed using a solid block. In another embodiment of the invention, an electrode may be deposited as a layer directly onto the dielectric. In one aspect, an electrode may be formed using a conductive paint.

In an embodiment of the invention, a plasma is obtained in a dielectric barrier discharge (DBD) when during one phase of the applied alternating voltage, charges accumulate between the dielectric surface and the opposing electrode until the electric field is sufficiently high enough to initiate an electrical discharge through the gas gap (also known as "gas breakdown"). During an electrical discharge, an electric field from the redistributed charge densities may oppose the applied electric field and the discharge is terminated. In one aspect, the applied voltage-discharge termination process may be repeated at a higher voltage portion of the same phase of the applied alternating voltage or during the next phase of the applied alternating voltage.

In another embodiment of the invention, a corona discharge scheme may be used (E. M. van Veldhuizen, W. R. Rutgers. "Corona Discharges: fundamentals and diagnostics" Invited Paper, Proceedings of Frontiers in Low Temperature Plasma Diagnostics IV, Rolduc, The Netherlands, March 2001, pp. 40–49). In one embodiment, a corona discharge scheme may use asymmetric electrodes. In one aspect of the invention, a discharge develops within a high electric field region near the area of strongest curvature of a sharp electrode. If the applied voltage or electrode gap distance is such that the discharge cannot transverse the gas gap, then the resulting corona discharge will be limited by electron recombination and space charge diffusion. In one embodiment of the invention, the tip of a probe, cannula or pin tool can serve as the region of strongest curvature and resulting high electric field to initiate a corona discharge.

Depending on the geometry and gas used for the plasma device, the applied voltages can range from 500 to 20,000 peak Volts, with frequencies ranging from line frequencies of 50 Hertz up to 20 Megahertz. In an embodiment of the invention, the frequency of a power source may range from 50 Hertz up to 20 Megahertz. In another embodiment of the invention, the voltage and frequency may range from 5,000 to 15,000 peak Volts and 50 Hertz to 50,000 Hertz, respectively. By way of a non-limiting example, such parameters of voltage and frequency are commonly found in neon sign ballasts for lighting purposes (Universal Lighting Technologies, Inc, Nashville, Tenn.).

Dielectric materials useful in the present invention include, but are not limited to, ceramic, glass, plastic, polymer epoxy, or a composite of one or more such materials, such as fiberglass or a ceramic filled resin (Cotronics Corp., Wetherill Park, Australia). In one embodiment, a ceramic dielectric is alumina. In another embodiment, a ceramic dielectric is a machinable glass ceramic (Corning Incorporated, Corning, N.Y.). In one embodiment of the invention, a glass dielectric is a borosilicate glass (Corning Incorporated, Corning, N.Y.). In another embodiment, a glass dielectric is quartz (GE Quartz, Inc., Willoughby, Ohio). In one embodiment of the invention, a plastic dielectric is polymethyl methacrylate (PLEXIGLASS and LUCITE, Dupont, Inc., Wilmington, Del.). In yet another embodiment of the invention, a plastic dielectric is polycarbonate (Dupont, Inc., Wilmington, Del.). In still another embodiment, a plastic dielectric is a fluoropolymer (Dupont, Inc., Wilmington, Del.). Dielectric materials useful in the present invention typically have dielectric constants ranging between 2 and 30.

The gas used in a plasma device of the invention can be ambient air, pure oxygen, any one of the rare gases, or a combination of each such as a mix of air or oxygen with argon and/or helium. Also an additive can be added to the gas, such as hydrogen peroxide, to enhance specific plasma cleaning properties.

FIG. 1 shows a cross section of a representative example of the DBD plasma cleaning device. In one embodiment, a dielectric includes a hollow open ended dielectric channel 101, with a thickness W from about 0.5 mm to about 3 mm and a length L from about 1 cm to about 5 cm. Coupled to the outside of the dielectric is an electrode 102, with an arbitrary thickness and a length I of about 0.5 to about 4 cm, which is connected to an AC power supply 104. The exact dimensions of dielectric channel 101 are dependent on the properties of the materials used for fabrication. In an embodiment of the invention, the dielectric constant and dielectric strength of a material may allow larger or smaller lengths and/or thicknesses of such materials used in the present invention.

In one embodiment, a plasma cleaning device of the invention is cylindrical. In another embodiment of the invention, a plasma cleaning device is rectangular. In yet another embodiment, a plasma cleaning device of the invention is elliptical. In still another embodiment of the invention, a plasma cleaning device of the invention is polygonal. Referring to FIG. 1, in one embodiment of the invention, the end of a grounded fluid handling device 103 is inserted into the dielectric channel to a point in between electrode 102 at the midpoint of length I of electrode 102, and acts as the opposing electrode. Plasma is thereby formed in between the outer surface of the fluid handling device 103 and the inner walls of the dielectric channel 101. In one embodiment, a plasma is a dielectric barrier discharge plasma. In another embodiment, a plasma is a corona discharge plasma. The free space H between the top and bottom edges of electrode 102 and the top and bottom edges of dielectric channel 101 is spaced a sufficient distance to prevent arcing between electrode 101 and fluid dispensing device 103, which in this embodiment acts as a ground. In one embodiment, the space is about 0.5 mm to about 10 mm to prevent arcing around the dielectric. In one embodiment, the minimum dimensions of space H may be determined as the distance required such that the corresponding electric field circumventing dielectric 101, but between electrodes 103 and 102, is not sufficient to induce a gas breakdown directly between 103 and 102. It will also be understood that the maximum dimension of space H may be determined by how far the tip of fluid handling device 103 can be inserted into the channel formed by dielectric 101.

Any volatized contaminants and other products from the plasma may be vented through the bottom of the device by coupling the bottom of the chamber formed by the dielectric to a region of negative pressure. In one embodiment, a region of negative pressure is a vacuum. In one aspect, a vacuum is in direct communication with a channel of the plasma device and is used to draw plasma products through the bottom of a plasma device of the invention.

Figure 2:
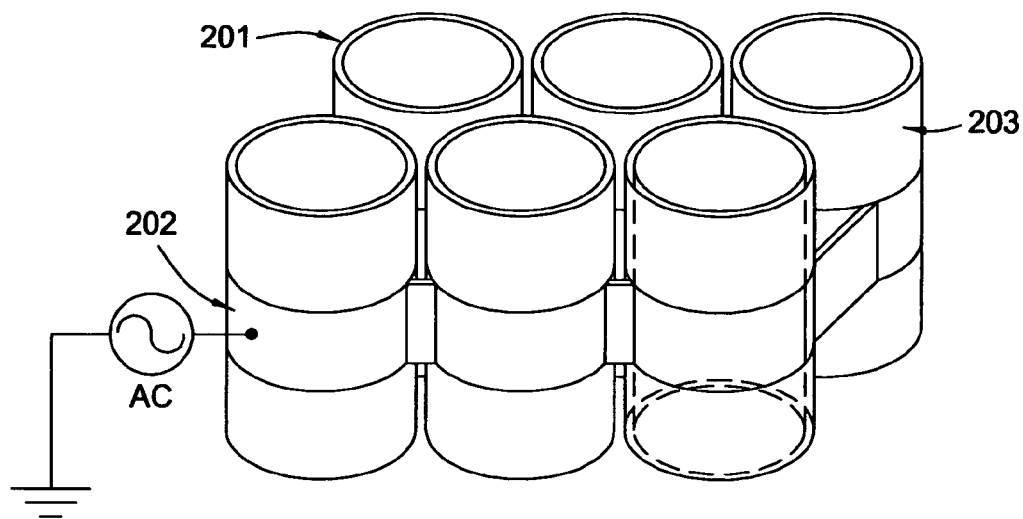
FIG. 2 is a top angle view of one embodiment of an atmospheric pressure plasma-based cleaning device of the invention.

FIG. 2 shows an embodiment of a representative DBD plasma cleaning device with a plurality of dielectric barrier discharge structures, with each individual plasma unit similar to that shown in FIG. 1. Outer surface 203 of the individual dielectric channels 201 are all coupled to a common outer electrode 202. In one embodiment, electrode 202 is connected to an AC power supply. In another embodiment of the invention, a power supply is a DC power supply. In one aspect, a DC power supply is pulsed and employs a square waveform. In another aspect, a DC power supply is pulsed and employs a sawtooth waveform.

A plurality of grounded fluid handling devices can be inserted in the plasma device and be simultaneously processed. The spacing between each of the individual plasma devices within the plurality are determined by the geometries of the fluid handling devices to be inserted. Typical geometries for dielectric structure 201 can follow those set by the Society for Biomolecular Engineering, Microplate Standards Development Committee for 96, 384, or 1536 well microplates (Publication ANSI/SBS 4-2004, "Well Positions for Microplates,", January 2004, The Society for Biomolecular Screening <<www.sbsonline.com>>). Other geometries include single opening units and openings in linear and two dimensional arrays.

Several procedures may be used to clean or sterilize the inner and outer surfaces of the fluid handling device. To clean, sterilize, or otherwise process the inner surfaces, the reactive and energetic components of the plasma are repeatedly aspirated into the fluid handling device, using the fluid handling devices' aspirating and dispensing capability, with the with aspiration volume, rate, and frequency determined by the desired amount of cleaning/sterilization required.

As shown in FIG. 1, in one embodiment of the invention, for cleaning or sterilizing the outer surfaces of a fluid handling device, the end of fluid dispensing device 103 can be inserted to a position before or at the top of electrode 102 to just clean the end of dispensing device 103, or it can be inserted to a position further below the top level of electrode 102 to clean the outer surfaces of the dispensing device. The period of time that the plasma is on and the reactive and energetic components are in contact with the surfaces is also determined by required processing parameters.

Figure 3:
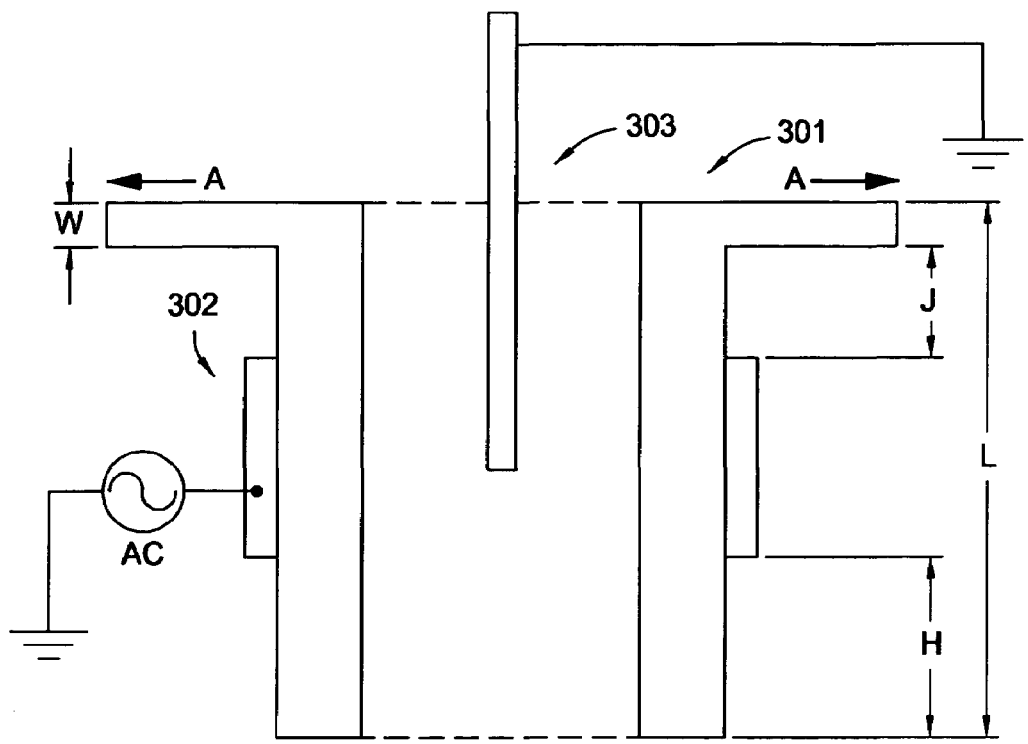
FIG. 3 is a cross section view of one embodiment of an atmospheric pressure plasma-based cleaning device of the invention, wherein the upper dielectric portion is extended perpendicularly outward.

In an embodiment of the present invention, the DBD plasma device may have its upper dielectric portion extended perpendicularly along Arrow A so that powered electrode 302 is also covered from the top as shown in the representative cross section in FIG. 3. This configuration allows the spacing J between electrode 302 and dielectric 301 to be smaller than the spacing H for the preventing of arcing around dielectric 301. In an embodiment of the invention, the minimum dimensions of space J may be determined as the distance required such that the corresponding electric field circumventing dielectric 301, and between electrode 302 and electrode 303, here the fluid handling device, is not sufficient to induce a gas breakdown directly between 303 and 302. In one embodiment, the maximum dimension of space J may be determined by how far the tip of fluid handling device 303 is inserted into a plasma cleaning device of the invention. In one embodiment of the invention, the tip of a fluid handling device 303 is situated midway in a plasma field. In another embodiment, the tip of a fluid handling device 303 is situated at about the center of a plasma field within a plasma cleaning device of the invention. In one aspect, the tip of a liquid handling device 303 is inserted into a plasma cleaning device to the midpoint of electrode 302. In another aspect, the tip of a fluid handling device 303 is placed within the region of maximum plasma density. The thickness W of dielectric 301 is similar to that discussed elsewhere herein with respect to FIG. 1. Furthermore, there can be no spacing J, such that the top of electrode 302 is adjacent to the bottom of perpendicularly extended dielectric 301. This will result in a plasma being created when the grounded fluid handling device is brought near to the top of dielectric 301 but still outside the dielectric channel.

Figure 4:
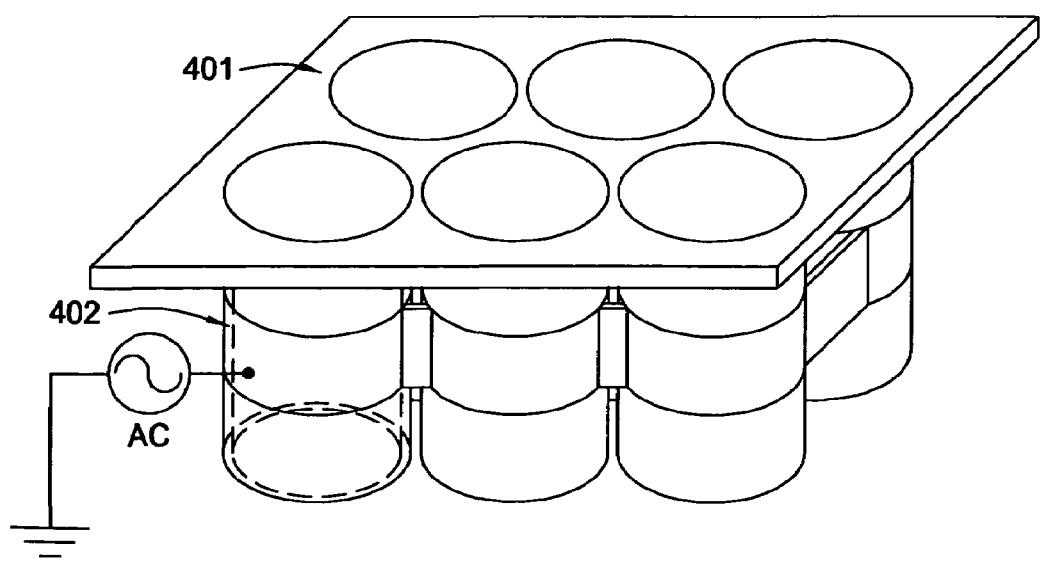
FIG. 4 is a top angle view of one embodiment of an atmospheric pressure plasma-based cleaning device of the invention, wherein the upper dielectric portion is extended perpendicularly outward.

FIG. 4 illustrates an embodiment of the invention including a plurality of DBD devices, each sharing a common extended upper dielectric 401 which covers common electrode 402 from the top.

Figure 5:
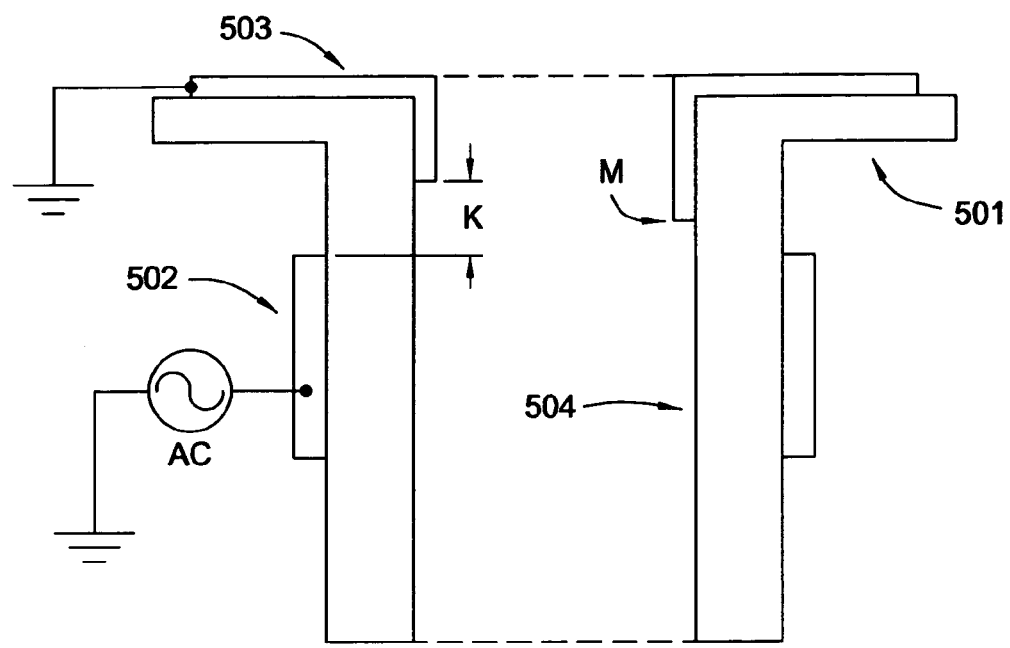
FIG. 5 is a cross section view of one embodiment of an atmospheric pressure plasma-based cleaning device of the invention, wherein a conducting surface is situated adjacent to the top of a perpendicularly outward extended dielectric.

In another embodiment of the invention, a conducting surface 503 of any thickness can be placed adjacent to the top of the perpendicularly extended dielectric. FIG. 5 shows a cross section of one embodiment of a representative design with a hole in conducting surface 503 aligned with the opening in dielectric surface 501. As shown in FIG. 5, inner edge M of conducting surface 503 can vertically cover inner dielectric wall 504 of dielectric 501 in addition to the top of the opening of dielectric 501. If conducting surface 503 is grounded, a plasma can now be formed in between the space K between the top of powered electrode 502 and inner edge M of grounded electrode 503. Referring to FIG. 5, in one embodiment of the invention, the maximum distance of space K may be determined wherein the electric field between edge M of electrode 503 located within the channel formed by dielectric 501 and inner dielectric wall 504 corresponding to the top of 502 is sufficient to allow for gas breakdown and the formation of a plasma within the channel formed by dielectric 501.

In one embodiment of the invention, the minimum distance of space K may be zero. In another embodiment of the invention, the minimum distance of space K may be a value greater than zero. The optimization of space K facilitates the creation of a more uniform and diffuse volumetric plasma inside the cylindrical channel formed by dielectric 501 when a grounded fluid handling device is inserted. In one embodiment of the invention, K is a distance between zero mm and 20 mm. In one aspect, K is a distance between 1 mm and 10 mm. In an embodiment of the invention, K is about 3 mm.

In one embodiment of the invention, conducting surface 503 can be left unconnected from ground by a switch so as to not have it participate as an electrode during the plasma cleaning/sterilization process. This will facilitate the creation of a more concentrated plasma at the extreme end of the fluid handling device as opposed to a diffuse volumetric plasma around the end.

Figure 6:
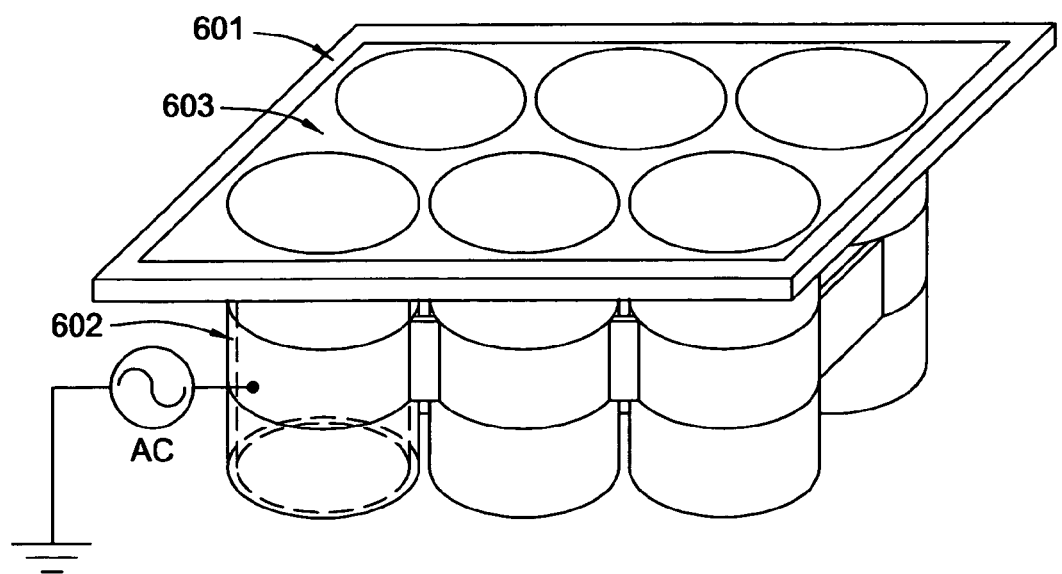
FIG. 6 is a top angle view of one embodiment of an atmospheric pressure plasma-based cleaning device of the invention, wherein a conducting surface is situated adjacent to the top of a perpendicularly outward extended dielectric.

FIG. 6 illustrates one embodiment of the invention, featuring a representative design of a plurality of DBD plasma devices sharing a common conducting surface 603, which can be grounded or ungrounded, and a common powered electrode 602, each separated by a common perpendicularly extended dielectric 601.

In an embodiment of the invention, a plurality of DBD plasma devices are arranged in a format of a microtiter plate. Examples of microtiter plate formats include, but are not limited to, a 96-well plate format, a 384-well plate format, and 1536-well plate format. However, it will be understood that plate formats having fewer than 96 wells, such as 48-well, 24-well, 12-well and 6-well formats, are also useful in the present invention. In one embodiment, the physical properties of a channel useful in the present invention, such as a channel formed by a well in a microtiter plate, can be determined based on the properties of the dielectric material used, the dimensions of such a channel, and the amount and character of energy used to produce a plasma within such a channel, as described in detail elsewhere herein. Similarly, the amount and character of energy used to produce a plasma within a channel of the invention may be determined, as described in detail elsewhere herein, by analysis of the physical properties of such a channel and the properties of the dielectric material used.

In an embodiment of the invention, an array of liquid handling devices may also be in a format compatible with a microtiter plate. In another embodiment, an array of liquid handling devices compatible with a microtiter plate format may be cleaned using an apparatus or method of the present invention. Microtiter plate handling devices useful in the present invention include, but are not limited to those using an XYZ format for liquid handling, such as the TECAN GENESIS (Tecan, Durham, N.C.). Other microplate handling formats compatible with the present invention include those used with instruments such as the Beckman Coulter FX (Beckman Coulter, Fullerton, Calif.) and the TekCel TekBench (TekCel, Hopkinton, Mass.).

While the invention has been described in detail and with reference to specific embodiments thereof, it will be apparent to one skilled in the art that various changes and modifications can be made therein without departing from the spirit and scope thereof. Thus, it is intended that the present invention covers the modifications and variations of this invention provided they come within the scope of the appended claims and their equivalents. Further, each and every reference disclosed herein is hereby incorporated by reference in its entirety.

What is claimed is:

1. Apparatus for plasma cleaning, comprising:
   a plate having a conductive surface and an opposing dielectric surface, the plate having a plurality of openings extending through the conductive and dielectric surfaces;
   a plurality of hollow dielectric members coupled at a first end to the dielectric surface of the plate and extending in a direction opposite the conductive surface, each of the plurality of hollow dielectric members having a first opening at the first end aligned with a respective one of the plurality of openings in the plate; and
   an electrode coupled to a central portion of an outer surface of each of the hollow dielectric members.

2. The apparatus of claim 1, wherein the conductive surface of the plate further comprises an extension that protrudes into at least one of the plurality of hollow dielectric members along an inner surface thereof.

3. The apparatus of claim 2, wherein a distance measured along a central axis of the at least one hollow dielectric member and defined between a first end of the protruding extension of the conductive member and a proximate edge of the electrode is greater than or equal to zero.

4. The apparatus of claim 1, wherein the conductive surface is grounded.

5. The apparatus of claim 1, wherein a central axis of each of the plurality of hollow dielectric members are substantially parallel.

6. The apparatus of claim 1, wherein the hollow dielectric member is cylindrical.

7. The apparatus of claim 1, wherein the hollow dielectric member is a polygonal tube.

8. The apparatus of claim 1, further comprising:
a second opening formed through at least one of the hollow dielectric members proximate a second end of the hollow dielectric member opposite the first end.

9. The apparatus of claim 8, wherein the second opening is fluidly coupled to a negative pressure source adapted to draw plasma cleaning byproducts through the second opening.

10. The apparatus of claim 1, wherein the plurality of hollow dielectric members are arranged in a microliter plate format.

11. The apparatus of claim 1, further comprising a voltage source adapted to provide a voltage between about 5000 V to about 15000 V to the electrode.

12. The apparatus of claim 1, further comprising a voltage source adapted to provide a voltage having a frequency between about 50 Hz and about 14 MHz to the electrode.

13. The apparatus of claim 1, further comprising a closed end of at least one of the hollow dielectric members opposite the first end.

* * * * *